(12) United States Patent  Unger

(10) Patent No.: US 12,589,214 B1
(45) Date of Patent: Mar. 31, 2026

(54) LARYNGEAL MASK AIRWAY WITH POSITIONING AND TEMPERATURE SENSORS

(71) Applicant: RUSKID LLC, Rancho Santa Fe, CA (US)

(72) Inventor: Richard Unger, Rancho Santa Fe, CA (US)

(73) Assignee: RUSKID LLC, Rancho Santa Fe, CA (US)

( * ) Notice: Subject to any disclaimer, the term of this patent is extended or adjusted under 35 U.S.C. 154(b) by 0 days.

(21) Appl. No.: 19/228,604

(22) Filed: Jun. 4, 2025

(51) Int. Cl.
*A61M 16/04* (2006.01)

(52) U.S. Cl.
CPC . *A61M 16/0445* (2014.02); *A61M 2205/3368* (2013.01); *A61M 2205/50* (2013.01)

(58) Field of Classification Search
CPC .............. A61M 16/04; A61M 16/0402; A61M 16/0434; A61M 2205/3368
See application file for complete search history.

(56) References Cited

U.S. PATENT DOCUMENTS

| | | | | | |
|---|---|---|---|---|---|
| 2003/0000534 | A1* | 1/2003 | Alfery | ............... | A61M 16/0409 128/207.14 |
| 2010/0275919 | A1* | 11/2010 | Sung | ................... | A61M 16/161 128/204.22 |
| 2010/0300450 | A1* | 12/2010 | Barodka | ........... | A61M 16/0409 128/207.18 |

| | | | | | |
|---|---|---|---|---|---|
| 2011/0190596 | A1* | 8/2011 | Hacker | ............. | A61M 16/0488 600/301 |
| 2012/0172749 | A1* | 7/2012 | He | .................... | A61M 16/0409 600/549 |
| 2013/0281885 | A1* | 10/2013 | Rowbottom | ......... | A61B 5/0215 600/587 |
| 2019/0262563 | A1 | 8/2019 | Kwok | | |
| 2023/0372032 | A1 | 11/2023 | Gomley et al. | | |
| 2024/0157076 | A1* | 5/2024 | Schaner | ................. | A61B 1/267 |
| 2025/0090780 | A1* | 3/2025 | Lafreniere | ........ | A61M 16/0434 |

FOREIGN PATENT DOCUMENTS

| | | | | | |
|---|---|---|---|---|---|
| CN | 108853671 | A | * 11/2018 | ............ | A61M 16/04 |
| GB | 2611046 | A | * 3/2023 | .......... | A61B 5/4836 |
| WO | 2018125841 | A1 | 7/2018 | | |
| WO | 2023047109 | A1 | 3/2023 | | |

* cited by examiner

*Primary Examiner* — Colin W Stuart
*Assistant Examiner* — Douglas Y Sul
(74) *Attorney, Agent, or Firm* — DLA Piper LLP (US)

(57) ABSTRACT

Embodiments disclosed herein are directed to an improved LMA with a positioning sensor and a temperature sensor at the posterior dome of the mask of the LMA. The positioning sensor provides positioning measurements for the clinician to determine that the LMA is correctly positioned with the posterior dome in contact with the hypopharyngeal wall. With this correct positioning of the LMA, a temperature sensor—either on the same chip as the positioning sensor or nearby the positioning sensor—has a stable mucosal contact with the hypopharyngeal wall to measure the patient's core temperature. Therefore, the improved LMA provide at least the twin benefits: ensuring that the LMA is correctly positioned and ensuring that the measured core temperature is valid.

19 Claims, 6 Drawing Sheets

100

450

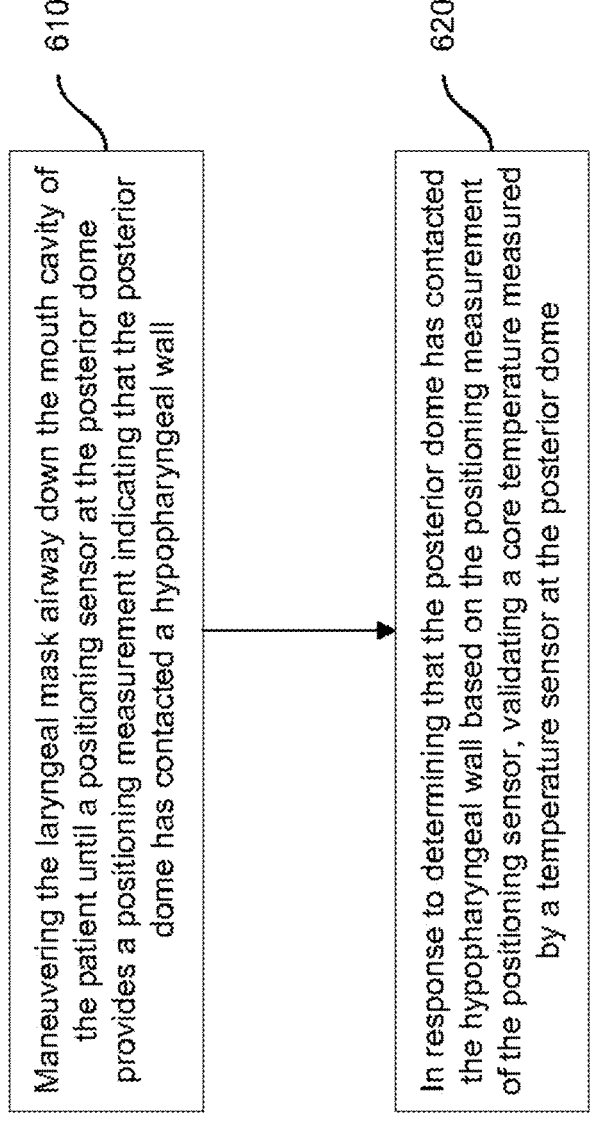

Maneuvering the laryngeal mask airway down the mouth cavity of the patient until a positioning sensor at the posterior dome provides a positioning measurement indicating that the posterior dome has contacted a hypopharyngeal wall

610

In response to determining that the posterior dome has contacted the hypopharyngeal wall based on the positioning measurement of the positioning sensor, validating a core temperature measured by a temperature sensor at the posterior dome

LARYNGEAL MASK AIRWAY WITH POSITIONING AND TEMPERATURE SENSORS

FIELD OF THE INVENTION

This disclosure relates to improved laryngeal mask airways (LMAs, singular form: LMA) with positioning and temperature sensors, and airway systems that use the improved LMAs.

BACKGROUND INFORMATION

LMAs are medical devices that are used to maintain an open airway in unconscious or anesthetized patients. LMAs are also used to administer anesthesia. An LMA includes a curved airway tube that connects to an air source and an elliptical mask with a cuff at the distal end. Once the LMA is in the desired supraglottic position at or near the upper esophageal sphincter, the cuff is inflated to form a seal that allows for positive pressure ventilation when needed (e.g., anesthesia or machine bag-valve-mask. In spontaneously breathing patients, the LMA maintains airway patency without positive pressure.

While LMAs have been hugely successful, further improvements are desired.

SUMMARY OF THE INVENTION

Embodiments disclosed herein are directed to an improved LMA with a positioning sensor and a temperature sensor at the posterior dome of the mask of the LMA. The positioning sensor provides positioning measurements for the clinician to determine that the LMA is correctly positioned with the posterior dome in contact with the hypopharyngeal wall. With this correct positioning of the LMA, a temperature sensor—either on the same chip as the positioning sensor or nearby the positioning sensor—has a stable mucosal contact with the hypopharyngeal wall to measure the patient's core temperature. In some embodiments, the positioning sensor may include a contact sensor (e.g., capacitive or resistive film sensor) and the temperature sensor may include a thermistor. These sensors may be fabricated on a single chip (e.g., application specific integrated circuit (ASIC)) or placed adjacent to one another to validate placement and temperature in real-time. Therefore, the improved LMA provide at least the twin benefits: ensuring that the LMA is correctly positioned and ensuring that the measured core temperature is valid.

In some embodiments, a laryngeal mask airway comprises a mask with a posterior dome configured to contact a hypopharyngeal wall of a patient; a temperature sensor at the posterior dome, the temperature sensor configured to measure a core temperature of the patient at the hypopharyngeal wall; and a positioning sensor at the posterior dome, the positioning sensor configured to provide a positioning measurement that can be used to determine whether the posterior dome has contacted the hypopharyngeal wall.

In some embodiments, a method of positioning laryngeal mask airway and measuring a patient's core temperature comprises maneuvering the laryngeal mask airway, having a mask with posterior dome, down the mouth cavity of the patient until a positioning sensor at the posterior dome provides a positioning measurement indicating that the posterior dome has contacted a hypopharyngeal wall; and in response to determining that the posterior dome has contacted the hypopharyngeal wall based on the positioning measurement of the positioning sensor, validating a core temperature measured by a temperature sensor at the posterior dome.

In some embodiments airway system comprises a mask with a posterior dome configured to contact a hypopharyngeal wall of a patient; a temperature sensor at the posterior dome, the temperature sensor configured to measure a core temperature of the patient at the hypopharyngeal wall; a positioning sensor at the posterior dome, the positioning sensor configured to provide a positioning measurement that can be used to determine whether the posterior dome has contacted the hypopharyngeal wall; and a computing device configured to wirelessly receive the measured core temperature and the positioning measurement.

BRIEF DESCRIPTION OF DRAWINGS

FIG. 6 depicts a flowchart of an example method of positioning a LMA and measuring a patient's core temperature, based on the example embodiments of this disclosure.

It should be understood that the above Figures are for illustrative purposes only, and therefore should not be considered limiting.

DETAILED DESCRIPTION OF THE INVENTION

Figure 1:
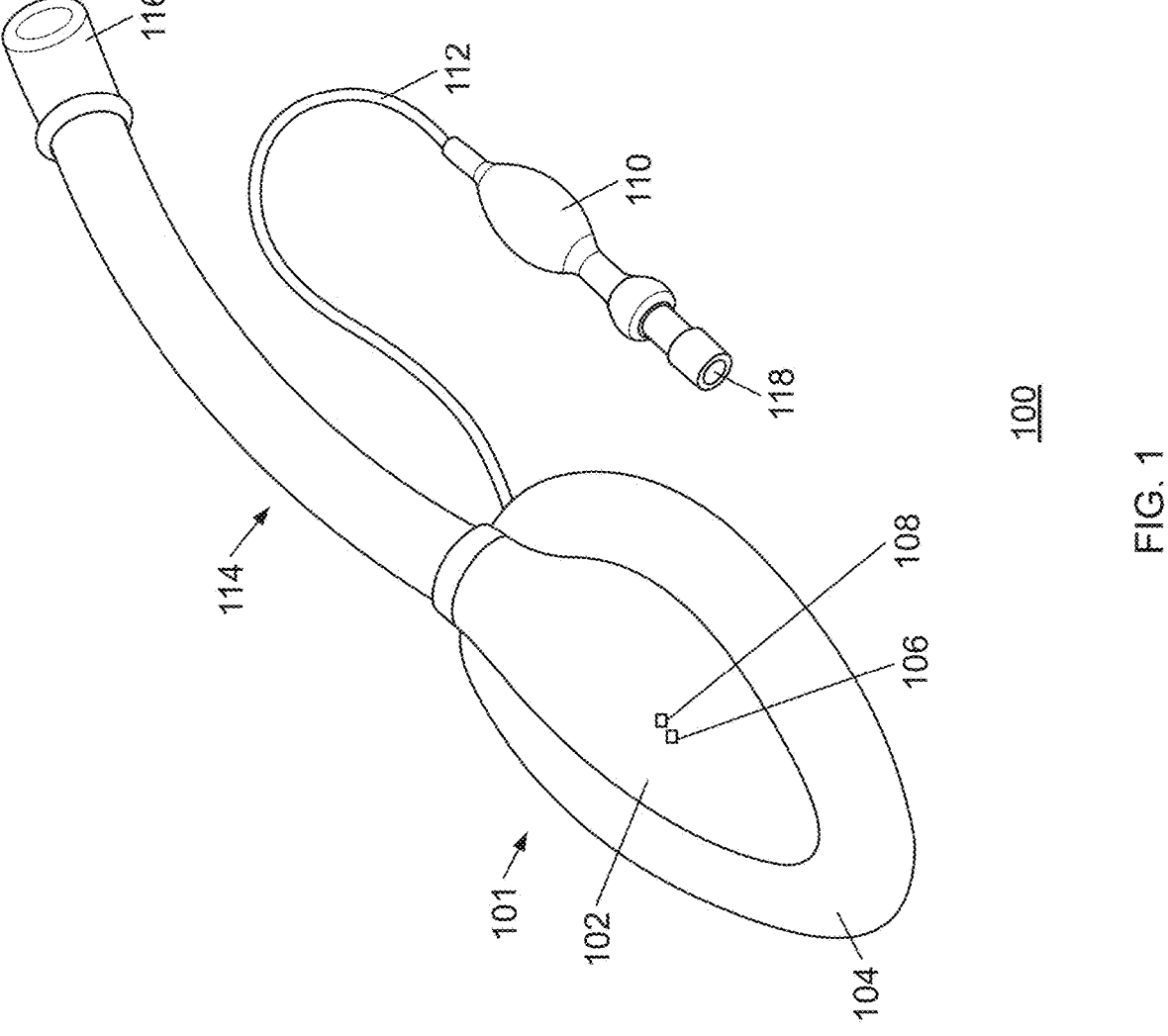
FIG. 1 depicts an example LMA, based on the example embodiments of this disclosure.

FIG. 1 depicts an example LMA 100, based on the example embodiments of this disclosure. As shown, the LMA 100 may generally include a mask 101 and an airway tube 114. The mask 101 may include a posterior dome 102 that will be in contact with the hypopharyngeal wall when the LMA 100 is in situ (i.e., at the deployed position). The airway tube 114 may be connected to an air supply at the proximal end 116. The airway tube 114 may also be used to administer anesthesia to the patient, where the anesthesia is supplied from the proximal end 116.

The mask 101 may include a cuff 104 that may press against the patient's anatomy (e.g., at or near the upper esophageal sphincter) for a stable positioning of the LMA 100. In some embodiments, the cuff 104 may be air-filled. In these embodiments, an inflation line 112 may provide the air to the cuff. This air may be received at the proximal end 118, e.g., through a syringe. An inflation pilot balloon 110 may allow the clinician to gauge the pressure within the air-filled cuff 104. In some embodiments, the cuff 104 may be gel-filled.

Figure 2:
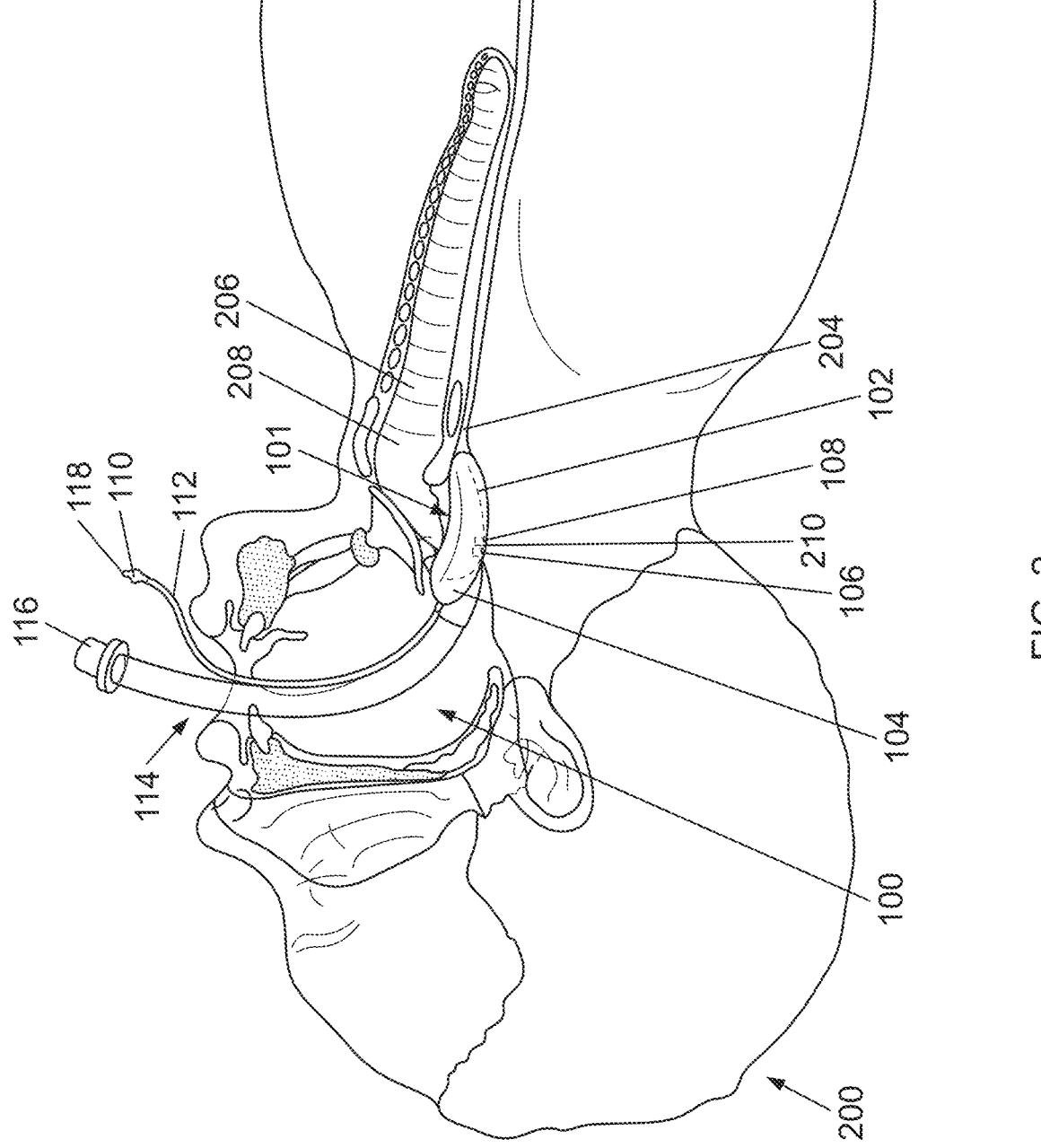
FIG. 2 depicts the LMA in the deployed position within the patient, according to example embodiments of this disclosure.
Figure 3:
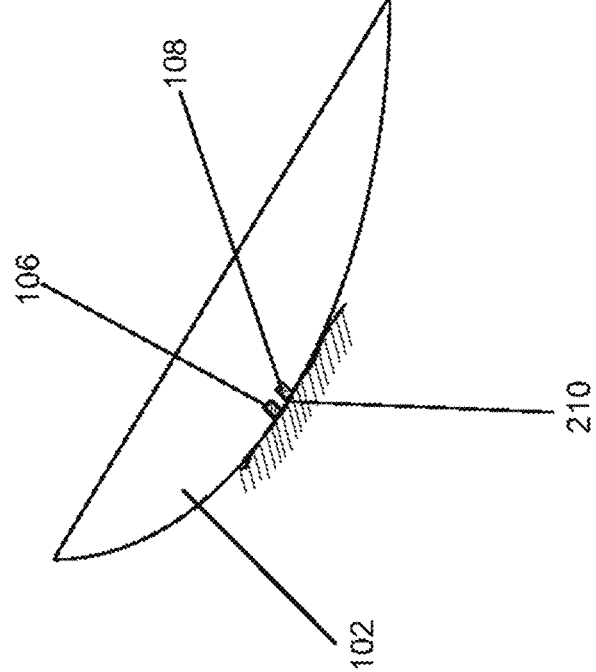
FIG. 3 depicts a contact between the posterior dome and the hypopharyngeal wall with the LMA is in situ, according to example embodiments of this disclosure.

The mask 101 may include a posterior dome 102 that is in contact with the hypopharyngeal wall when the LMA 100 is in situ (as shown in FIGS. 2 and 3 below). A positioning sensor 106 may be provided within the posterior dome 102. The positioning sensor 106 may include any type of sensor that may indicate the position of the posterior dome 102 vis-à-vis the hypopharyngeal wall. The positioning sensor 106, for example, may include a contact sensor that may determine whether the posterior dome 102 has contacted the hypopharyngeal wall. The indications from the contact sensor may be binary: contact/or no contact. In some embodiments, the contact sensor may include a capacitive or resistive thin-film sensor. In some embodiments, the positioning sensor 106 may include a pressure sensor. The pressure sensor may measure the pressure exerted by the hypopharyngeal wall against the posterior dome 102. When the measured pressure is above a predetermined threshold, a clinician (or a device) may determine that the posterior dome 102 has contacted the hypopharyngeal wall. In some embodiments, the positioning sensor 106 may include a mucus sensor. The mucus sensor may be configured for the specific type of mucus in the hypopharyngeal wall, and when a measurement of the specific type of mucus is above a threshold, the mucus sensor may indicate that the posterior dome 102 has contacted the hypopharyngeal wall. In other embodiments, the positioning sensor 106 may include an inertial measurement unit. The inertial measurement unit may measure the acceleration, angular rate, and/or any other inertial parameter of the unit as the posterior dome 102 advances within the patient. A predetermined measurement from the inertial measurement unit may indicate that the posterior dome 102 is in contact with the hypopharyngeal wall. In some embodiments, the positioning sensor 106 may include an accelerometer. The accelerometer may also measure the mechanical movement of the positioning sensor 106 and a predetermined measurement may indicate the posterior dome 102 has contacted the hypopharyngeal wall. Generally, any kind of positioning sensor 106 that may measure the position of the posterior dome 102 with respect to the hypopharyngeal wall should be considered within the scope of this disclosure.

The posterior dome 102 contacting the hypopharyngeal wall may indicate that the LMA 100 is correctly positioned within the patient. The correct positioning is supraglottic, wherein the LMA 100 is positioned at or near the upper esophageal sphincter of the patient (as shown in FIG. 2 below). The correct positioning of the LMA 100 is based on the contact between the posterior dome 102 and the hypopharyngeal wall can provide an accurate core temperature measurement of the patient. Accordingly, a temperature sensor 108 is provided at the posterior dome 102.

The temperature sensor 108 may include any type of sensor that may perform real-time temperature measurement of the hypopharyngeal wall. For instance, the temperature sensor 108 may include a thermistor. The thermistor may be a type of resistor whose resistance changes predictably with temperature. That is, a measured resistance may correspond to a particular temperature. In other embodiments, the temperature sensor 108 may include a resistance temperature detector. The resistance temperature detector also uses changes in electrical resistance of a material based on the changes in temperature to measure the temperature of the hypopharyngeal wall (i.e., the core temperature through the hypopharyngeal wall). In other embodiments, the temperature sensor 108 may include a thermocouple. The thermocouple may be a temperature-sensing device that may measure temperature by converting thermal energy into an electrical signal. In some embodiments, the temperature sensor 108 may include a semiconductor temperature sensor, which may be an electronic device that measures temperature using temperature-dependent characteristics of semiconductor materials such as diodes. Generally, any type of temperature sensor temperature sensor 108 for measuring the core temperature of the patient when the LMA 100 is in situ should be considered within the scope of this disclosure.

The example the positioning sensor 106 and the temperature sensor 108 being separate units in FIG. 1 is just for the purpose of illustration only, and should not be considered limiting. In some embodiments, the positioning sensor 106 and the temperature sensor 108 may be fabricated on a single chip, e.g., ASIC) and/or any other type of semiconductor chip. In the embodiments where the positioning sensor 106 and the temperature sensor 108 are separate units, theses sensors are sufficiently close to each other such that the contact confirmation determined from the positioning sensor 106 may be used to validate the temperature measurement from the temperature sensor 108. That is, as the clinician is confident that the positioning sensor 106 has indicated that the posterior dome 102 has a stable mucosal contact with the hypopharyngeal wall, the temperature measurement from the nearby temperature sensor 108 is valid as well.

One or more of the positioning sensor 106 and the temperature sensor 108 may provide their measurement data in real time, e.g., to an electronic device. The electronic device may include any type of clinical or smart device that may receive the measurement data and/or display the same to the clinician. Using the real-time data from the positioning sensor 106, the clinician may determine whether the LMA 100 is correctly positioned when the clinician is maneuvering the LMA 100 through the patient's anatomy. In some embodiments, the electronic device may provide a visual (e.g., a screen turning green), an audible (e.g., a beep), and/or haptic (the device temporarily shaking) that the LMA 100 has been correctly positioned. Once the LMA 100 is correctly positioned, the clinician may further use the real time core temperature measurement for a real-time core temperature monitoring of the patient. This may be especially important for patients under general anesthesia who may be prone to hypothermia, inadvertent hypothermia, and/or malignant hyperthermia.

In some embodiments, one or more of the positioning sensor 106 and the temperature sensor 108 may be wireless. These sensors may therefore transmit the data wirelessly to the receiving clinical or smart device. Having wireless sensors may remove the complexity of maintaining extra wires with the LMA 100. However, this is just an example, and wired sensors may be used as well and are within the scope of this disclosure.

FIG. 2 depicts the LMA 100 in the deployed position within the patient 200, according to example embodiments of this disclosure. As shown, the LMA 100 (particularly the mask 101) is deployed near the upper esophageal sphincter 204. The LMA 100 is supraglottic as it is deployed above the glottis 208 of the trachea 206 area. As shown, the posterior dome 102 (shown in dotted line as the posterior dome 102 is behind the cuff 104) is in contact with the hypopharyngeal wall 210. The positioning sensor 106 (also shown in dotted line as it is behind the cuff 104) is also in contact with the hypopharyngeal wall 210 and may confirm this through the positioning measurement. The temperature sensor 108 (also shown in dotted line as it is behind the cuff 104)) is also in contact with (i.e., in stable mucosal contact with) the hypopharyngeal wall 210 such that accurate temperature measurements can be made. As described with respect to FIG. 1, the separate positioning sensor 106 and temperature sensor 108 is just for illustration only and these sensors can be within a single ASIC.

FIG. 3 depicts a contact between the posterior dome 102 and the hypopharyngeal wall 210 with the LMA 100 is in situ, according to example embodiments of this disclosure. As shown, the positioning sensor 106 is in contact with the hypopharyngeal wall 210 provides the measurements to indicate this contact. The temperature sensor 108 is also in contact (i.e., stable mucosal contact) with the hypopharyngeal wall 210 thereby providing reliable and clinically valid core temperature measurement.

Figure 4:
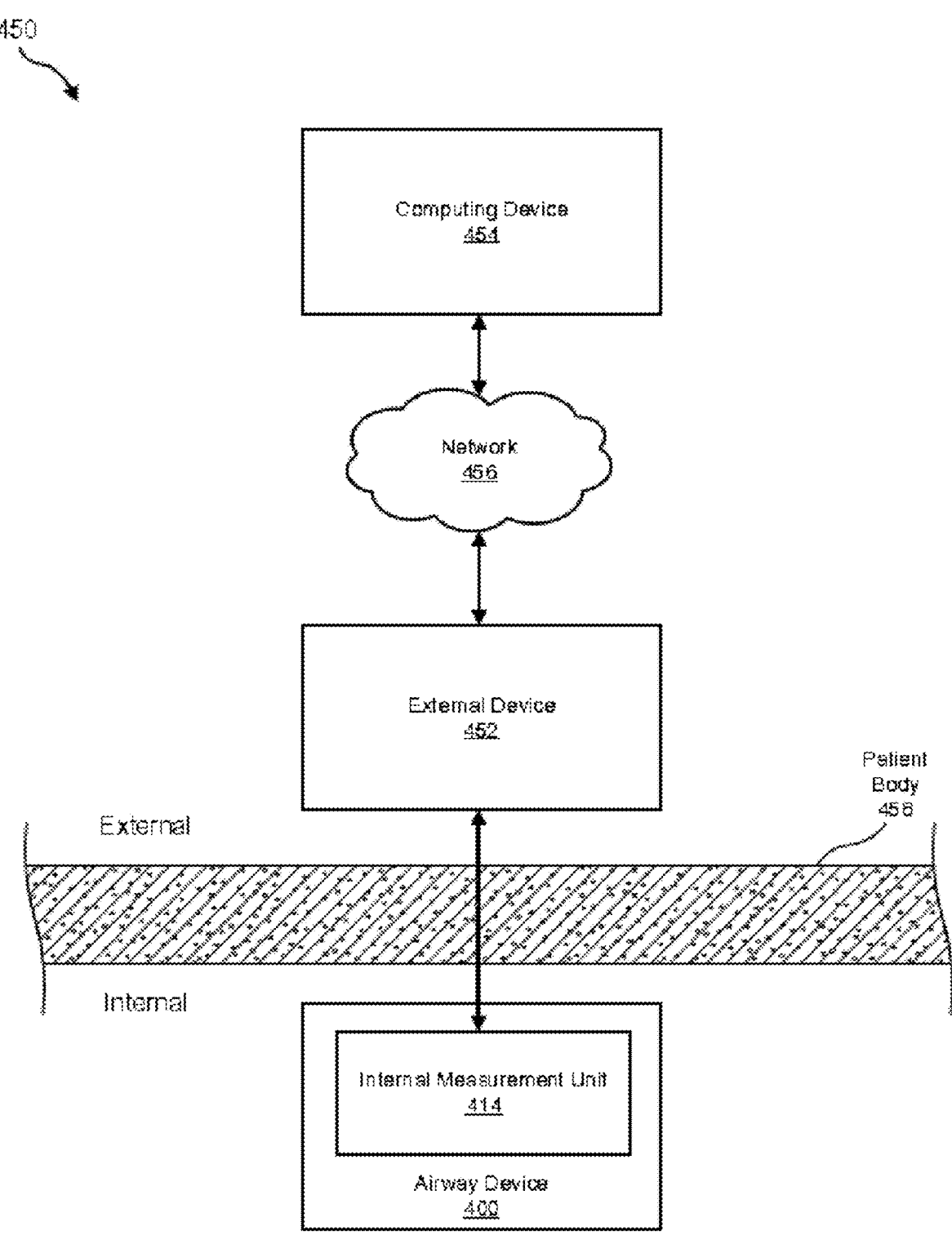
FIG. 4 depicts an example airway system, according to example embodiments of this disclosure.

FIG. 4 depicts an example airway system 450, according to example embodiments of this disclosure. As shown, the system 450 may include an airway device 400 (e.g., LMA 100 as described in FIGS. 1 and 2), at least a portion of which is disposed internally within a patient body 458. Airway device 400 may include an internal measurement unit 414, according to example embodiments of this disclosure.

The system 450 may also include an external device 452 that is disposed at a location external to the patient body 458. The external device 452 may include any suitable device that is accessible outside the patient body 458 and/or that is configured to send communication signals outside the patient body 458. The external device 452 may be located entirely or at least partially outside the patient body 458. For example, the external device 452 may be a wearable computing device and/or monitoring device that is mounted or otherwise secured directly or indirectly to the patient body 458. Additionally or alternatively, the external device 452 may include a computing device that is not coupled to the patient body 458. For example, external device 452 may be a patient monitoring device that may, for example, be positioned in close proximity to the patient body 458 within a range that is sufficiently close to receive and/or transmit communication signals wirelessly with at least a portion of a communication subsystem of the airway device 400. In some embodiments, the external device 452 may be held by a clinician.

At least a portion of the internal measurement unit 414 may be configured to communicate wirelessly with the external device 452 in any suitable manner, as described herein. The internal measurement unit 414 may be configured to transmit signals to and/or receive signals from the external device 452. In some embodiments, the internal measurement unit 414 may additionally or alternatively be configured to communicate wirelessly with one or more devices (e.g., external device 452) located outside the patient body 458 and/or with one or more devices located within or at least partially within the patient body 458 (e.g., one or more devices implanted or otherwise disposed within the patient body 458).

As shown in FIG. 4, the illustrative system 450 may also include a network 456 that is communicatively couple with the external device 452. The network 456 may be or may include one or more local and/or wide-area, wired and/or wireless networks, including a local-area or wide-area enterprise network and/or the Internet. Accordingly, the network 456 may be, for example, a hard-wired network (e.g., a local area network within a biopharma research office), a wireless network (e.g., connected over Wi-Fi, Bluetooth, and/or cellular networks), a cloud-based computing network, or any combination thereof. For example, in some embodiments, the external device 452 and one or more other devices, such as an additional computing device 454, may be located within the same building or building complex and connected directly to each other or connected to each other via the network 456. In some embodiments, the external device 452 and the additional computing device 454 may be integrated as one device or system.

The external device 452 may be any suitable one or more electronic devices configured to send instructions and/or information to the computing device 454 and/or the internal measurement unit 414 of the airway device 400, to receive information from the computing device 454 and/or the internal measurement unit 414, and/or to process obtained data. In some embodiments, the external device 452 may be a fixed electronic device such as a desktop computer, a rack-mounted computer, or any other suitable fixed electronic device. Alternatively, the external device 452 may be a portable device such as a laptop computer, a smart phone, a tablet computer, or any other portable device that may be configured to send instructions and/or information to the computing device 454 and/or the internal measurement unit 414, to receive information from the computing device 454 and/or the internal measurement unit 414, and/or to process obtained data. It should also be appreciated that in some embodiments, the external device 452 may communicate with classical computing hardware that is configured in any architecture.

The computing device 454 may be any suitable one or more electronic devices configured to send instructions and/or information to the external device 452, to receive information from the external device 452, and/or to process obtained data. In some embodiments, the computing device 454 may be a fixed electronic device such as a desktop computer, a rack-mounted computer, or any other suitable fixed electronic device. Alternatively, the computing device 454 may be a portable device such as a laptop computer, a smart phone, a tablet computer, or any other portable device that may be configured to send instructions and/or information to the external device 452, to receive information from the external device 452, and/or to process obtained data.

The external device 452 and/or the computing device 454 can include a client interface for interfacing with a client (e.g., a clinician, a patient caregiver, etc.). In some embodiments, the client interface may include one or more graphical user interfaces. In some embodiments, client interface may include executable instructions. A client can interact with the external device 452 and/or the computing device 454 via a client interface to control or configure internal measurement unit 414 and/or any other suitable portion of the airway device 400, the external device 452, and/or the computing device 454. Additionally or alternatively, a client can use a client interface to view data generated by the internal measurement unit 414, the external device 452, and/or the computing device 454. In some examples, the internal measurement unit 414 may generate data based on signals received from the temperature sensor 108 and/or the positioning sensor 106 of the internal measurement unit 414. Additionally or alternatively, external device 452 and/or computing device 454 may generate data based on signals and/or data received from internal measurement unit 414 of airway device 400.

In some embodiments, the internal measurement unit 414, the external device 452, and/or computing device 454 may generate data based on analysis of one or more signals received from the sensors 106, 108 of internal measurement unit 414. Signals received from sensors 106, 108 of the internal measurement unit 414 and/or data generated by the internal measurement unit 414, the external device 452, and/or the computing device 454 may be utilized in any suitable manner. For example, such signals and/or generated data may be utilized in a feedback loop of a system maintaining a patient's state to adjust and/or maintain one or more parameters affecting the patient's state. Additionally or alternatively, such signals and/or generated data may be presented in a suitable manner via a client interface of, for example, the external device 452 and/or the computing device 454.

Figure 5:
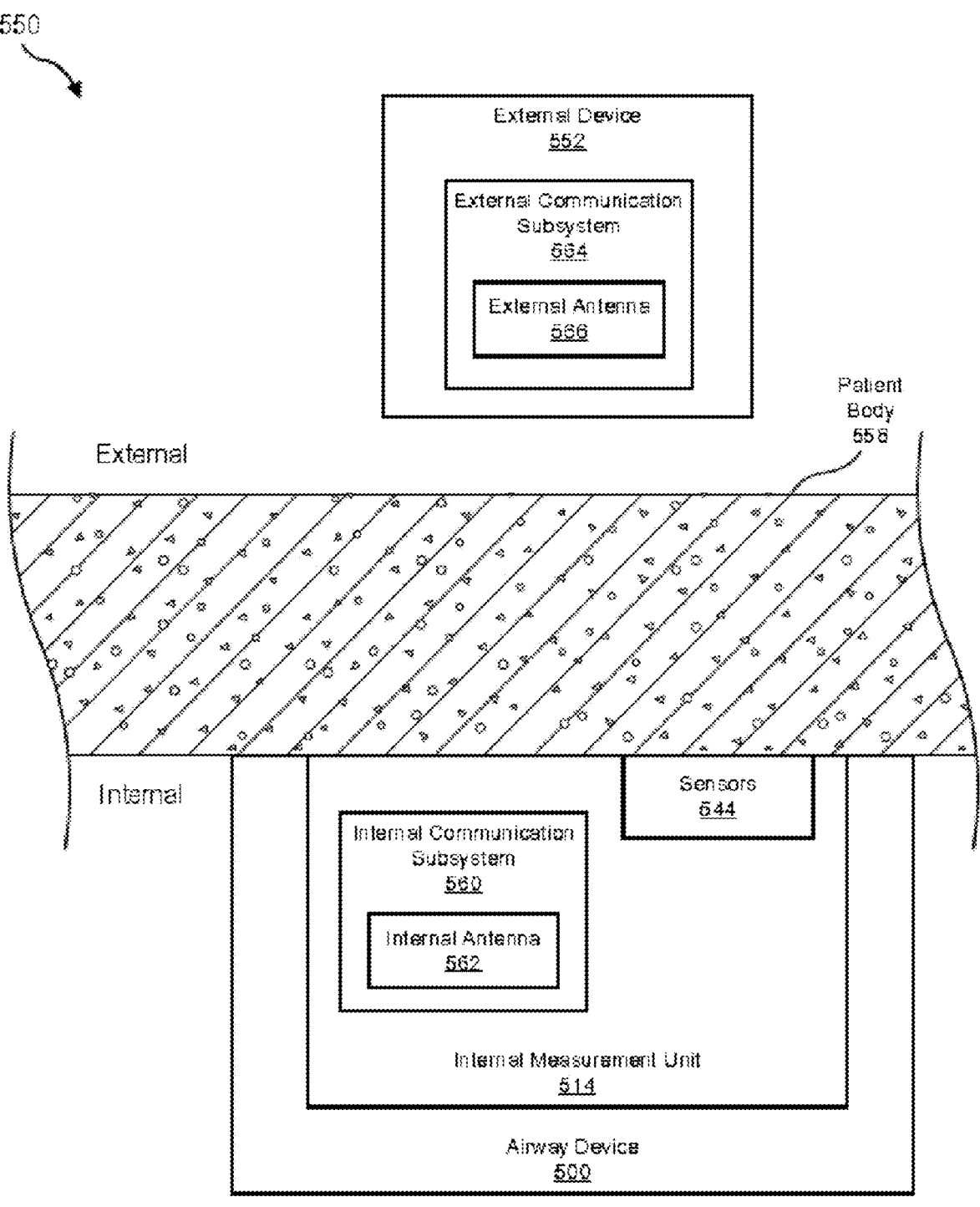
FIG. 5 depicts an example airway system, according to example embodiments of this disclosure.

FIG. 5 depicts an example airway system 550, according to example embodiments of this disclosure. As illustrated, at least a portion of an airway device 500 (e.g., LMA 100 shown in FIGS. 1 and 2) may be positioned internally within a patient body 558 of a patient (see, e.g., FIG. 2). The airway device 500 may include an internal measurement unit 514 in accordance with embodiments disclosed herein. The internal measurement unit 514 may include an internal communication subsystem 560 and one or more sensors 544 (e.g., a positioning sensor 106 and a temperature sensor 108).

The internal communication subsystem 560 may be configured to wirelessly communicate with—to transmit the measurements from the positioning sensor 106 and the temperature sensor 108—one or more computing devices located outside of the patient body 558. The communication may be real-time communication. The internal communication subsystem 560 may include at least one internal antenna 562 for transmitting and/or receiving signals. Additionally, the external device 552 may include an external communication subsystem 564 having at least one external antenna 566 for transmitting and/or receiving signals. For example, the internal antenna 562 may transmit radio frequency (RF) waves that are received by the external antenna 566. Additionally, the external antenna 566 may transmit RF waves that are received by the internal antenna 562. RF waves transmitted and/or received by the internal antenna 562 and the external antenna 566 may be within any suitable RF band within an RF spectrum of from approximately 3 kHz to 300 GHz.

FIG. 6 depicts a flowchart of an example method 600 of positioning a LMA and measuring a patient's core temperature, based on the example embodiments of this disclosure. It should be understood that the steps of the method 600 are just shown as examples and should not be considered limiting. Methods with additional, alternative, or fewer number of steps should be considered within the scope of this disclosure. As described above, the LMA includes a mask with a posterior dome having a positioning sensor and a temperature sensor.

The method may begin at step 610, where the LMA may be maneuvered (e.g., by a clinician) down the mouth cavity of the patient until the positioning sensor at the posterior dome provides a positioning measurement indicating that the posterior dome has contacted a hypopharyngeal wall. Such indication confirms that the LMA is now in situ at the correct position.

At step 620, in response to determining that the posterior dome has contacted the hypopharyngeal wall based on the positioning measurement of the positioning sensor (i.e., the LMA is now in situ at the correct position), the core temperature measured by the temperature sensor is validated. Such validation means that the core temperature is an accurate measurement because the temperature sensor is now in stable mucosal contact with the hypopharyngeal as indicated by the positioning sensor.

Additional examples of the presently described method and device embodiments are suggested according to the structures and techniques described herein. Other non-limiting examples may be configured to operate separately or can be combined in any permutation or combination with any one or more of the other examples provided above or throughout the present disclosure.

It will be appreciated by those skilled in the art that the present disclosure can be embodied in other specific forms without departing from the spirit or essential characteristics thereof. The presently disclosed embodiments are therefore considered in all respects to be illustrative and not restricted.

The scope of the disclosure is indicated by the appended claims rather than the foregoing description and all changes that come within the meaning and range and equivalence thereof are intended to be embraced therein.

It should be noted that the terms "including" and "comprising" should be interpreted as meaning "including, but not limited to". If not already set forth explicitly in the claims, the term "a" should be interpreted as "at least one" and "the", "said", etc. should be interpreted as "the at least one", "said at least one", etc. Furthermore, it is the Applicant's intent that only claims that include the express language "means for" or "step for" be interpreted under 35 U.S.C. 112 (f). Claims that do not expressly include the phrase "means for" or "step for" are not to be interpreted under 35 U.S.C. 112 (f).

What is claimed is:

1. A laryngeal mask airway comprising:
   a mask with a posterior dome configured to contact a hypopharyngeal wall of a patient at a supraglottic position;
   a temperature sensor at the posterior dome, the temperature sensor configured to measure a core temperature of the patient at the hypopharyngeal wall; and
   a positioning sensor at the posterior dome and co-located with the temperature sensor, the positioning sensor configured to provide a binary positioning measurement that can be used to determine whether the posterior dome has contacted or not contacted the hypopharyngeal wall at the supraglottic position, wherein the determination of the posterior dome being contact with the hypopharyngeal wall based on the binary positioning measurement is used to validate the core temperature measurement from the temperature sensor.

2. The laryngeal mask airway of claim 1, wherein the temperature sensor is configured to wirelessly transmit the measured core temperature.

3. The laryngeal mask airway of claim 1, wherein the temperature sensor is configured to transmit the measured core temperature in real-time.

4. The laryngeal mask airway of claim 1, wherein the positioning sensor is configured to wirelessly transmit the positioning measurement.

5. The laryngeal mask airway of claim 1, wherein the positioning sensor is configured to transmit the positioning measurement in real-time.

6. The laryngeal mask airway of claim 1, wherein the temperature sensor is at least one of thermistor, a resistance temperature detector, a thermocouple, or a semiconductor sensor.

7. The laryngeal mask airway of claim 1, wherein the positioning sensor is at least one of a contact sensor, a mucus sensor, an inertial measurement unit, or an accelerometer.

8. The laryngeal mask airway of claim 1, wherein the temperature sensor and the positioning sensor are fabricated on a single chip.

9. The laryngeal mask airway of claim 1, wherein the temperature sensor and the positioning sensor are separate sensors.

10. A method of positioning laryngeal mask airway and measuring a patient's core temperature, the method comprising:
   maneuvering the laryngeal mask airway, having a mask with posterior dome, down the mouth cavity of the patient until a positioning sensor at the posterior dome provides a binary positioning measurement indicating that the posterior dome has contacted a hypopharyngeal wall at a supraglottic position; and in response to determining that the posterior dome has contacted the hypopharyngeal wall at the supraglottic position based on the positioning measurement of the positioning sensor, validating a core temperature measured by a temperature sensor co-located with the temperature sensor at the posterior dome.

11. The method of claim 10, further comprising:

wirelessly transmitting, by temperature sensor, the measured core temperature.

12. The method of claim 10, further comprising:

transmitting, by the temperature sensor in real-time, the measured core temperature.

13. The method of claim 10, further comprising:

wirelessly transmitting, by the positioning sensor, the positioning measurement.

14. The method of claim 10, further comprising:

transmitting, by the positioning sensor in real-time, the positioning measurement.

15. An airway system comprising:

a mask with a posterior dome configured to contact a hypopharyngeal wall of a patient;

a temperature sensor at the posterior dome, the temperature sensor configured to measure a core temperature of the patient at the hypopharyngeal wall at a supraglottic position;

a positioning sensor at the posterior dome and co-located with the temperature sensor, the positioning sensor configured to provide a binary positioning measurement that can be used to determine whether the posterior dome has contacted or not contacted the hypopharyngeal wall at the supraglottic position, wherein the determination of the posterior dome being contact with the hypopharyngeal wall based on the binary positioning measurement is used to validate the core temperature measurement from the temperature sensor; and a computing device configured to wirelessly receive the measured core temperature and the positioning measurement.

16. The system of claim 15, wherein the temperature sensor is at least one of thermistor, a resistance temperature detector, a thermocouple, or a semiconductor sensor.

17. The system of claim 15, wherein the positioning sensor is at least one of a contact sensor, a mucus sensor, an inertial measurement unit, or an accelerometer.

18. The system of claim 15, wherein the temperature sensor and the positioning sensor are fabricated on a single chip.

19. The system of claim 15, wherein the temperature sensor and the positioning sensor are separate sensors.

\* \* \* \* \*